(12) United States Patent
Burke

(10) Patent No.: US 6,546,747 B1
(45) Date of Patent: Apr. 15, 2003

(54) OBTAINING A REPRESENTATIVE SAMPLE OF LIQUIFIED REFRIGERANT AND ASSAYING ITS COMPOSITION

(76) Inventor: Frederico Burke, 1820 S. Edgewood Dr., Alhambra, CA (US) 91803

(*) Notice: Subject to any disclaimer, the term of this patent is extended or adjusted under 35 U.S.C. 154(b) by 0 days.

(21) Appl. No.: 10/108,009

(22) Filed: Mar. 26, 2002

(51) Int. Cl.[7] ............................................. F25B 43/00
(52) U.S. Cl. ........................... 62/475; 62/292; 62/474; 62/77
(58) Field of Search .................... 62/292, 475, 474, 62/77

(56) References Cited

U.S. PATENT DOCUMENTS

| | | | | |
|---|---|---|---|---|
| 5,425,242 A | * | 6/1995 | Dunne et al. | 62/85 |
| 5,582,014 A | * | 12/1996 | Lyon et al. | 62/606 |
| 5,620,502 A | * | 4/1997 | Dunne et al. | 95/142 |
| 5,749,245 A | * | 5/1998 | Thomas et al. | 62/623 |
| 6,016,661 A | * | 1/2000 | Sagar | 62/149 |
| 6,185,945 B1 | * | 2/2001 | Pfefferle et al. | 62/149 |
| 6,202,433 B1 | * | 3/2001 | Murry et al. | 62/292 |
| 6,260,372 B1 | | 7/2001 | Burke | |

* cited by examiner

Primary Examiner—William C. Doerrler
Assistant Examiner—Mark Shulman
(74) Attorney, Agent, or Firm—Donald D. Mon

(57) ABSTRACT

Assaying of liquid samples of refrigerant to determine their composition utilizing refractive index techniques. The sampling may be done with the use of extractors which remove refrigerant gases from refrigerant machines, and clean and dry the sample before it is assayed.

3 Claims, 1 Drawing Sheet

OBTAINING A REPRESENTATIVE SAMPLE OF LIQUIFIED REFRIGERANT AND ASSAYING ITS COMPOSITION

FIELD OF THE INVENTION

Obtaining from an existing refrigeration machine a representative sample of its refrigerant fluid in the liquid phase, and assaying the sample using refractive index techniques.

BACKGROUND OF THE INVENTION

The refrigerating cycle which mechanically compresses gaseous refrigerant into the liquid phase, and cools surroundings when the liquid is vaporized is famous and needs no explanation here. Halogenated carbon compounds such as CFC's, while ideal for refrigerant purposes, have proved to be a profound risk to the environment. For this reason their release into the atmosphere is generally forbidden.

The places the owner of a refrigerant system, especially of large air conditioning systems in a quandary. He can, of course, hire a collection service to remove all of the gases and replace them with others of known composition, but this is an economic cost which should be avoided if possible.

If a complete recharge is to be avoided by adding make-up gas, the question is what kind of gas to add to the system. There are many kinds of refrigerant gases available, and the owner has no reliable way to know what is actually there especially in older systems. It is unwise to mix unknown gases. A device, suitably portable, is needed to learn the constituent gases in the system being serviced.

Systems have been proposed to assay the contents of a system, but have not provided a convenient and sufficiently accurate sample preparation and assaying technique. It is an object to provide such a system and method.

A known system to recover refrigerant gas for later disposal is shown in applicant's U.S. Pat. No. 6,620,372, issued Jul. 17, 2001. While it can remove the gases, it is not adapted to assay them, and especially not with the use of a refractive index analyzer.

BRIEF DESCRIPTION OF THE INVENTION

A sampling and assaying system according to this invention receives refrigerant fluid from a machine whose fluid is to be assayed. The fluid is preferably received in its liquid phase. If not, it must be converted to the liquid phase before being analyzed. After the fluid enters this system, it is filtered and de-acidified. Thereafter it passes through an oil separator, another filter, and a drier. At this point, the undesirable contaminants will have been removed. A pump removes the "purified" refrigerant, which now may be removed from the system for assay purposes.

According to this invention a refractive index analyzer is disposed between two selector valves, which can be set to permit the liquid to enter the analyzer. Alternatively, they can be set to direct the system fluid to a recovery tank.

Accordingly, this system can be utilized as a collector from the refrigeration machine for disposal elsewhere, or as an analyzer for successive analytical runs.

The above and other features of this invention will be fully understood from the following detailed description and the accompanying drawings, in which:

DETAILED DESCRIPTION OF THE INVENTION

Figure 1:
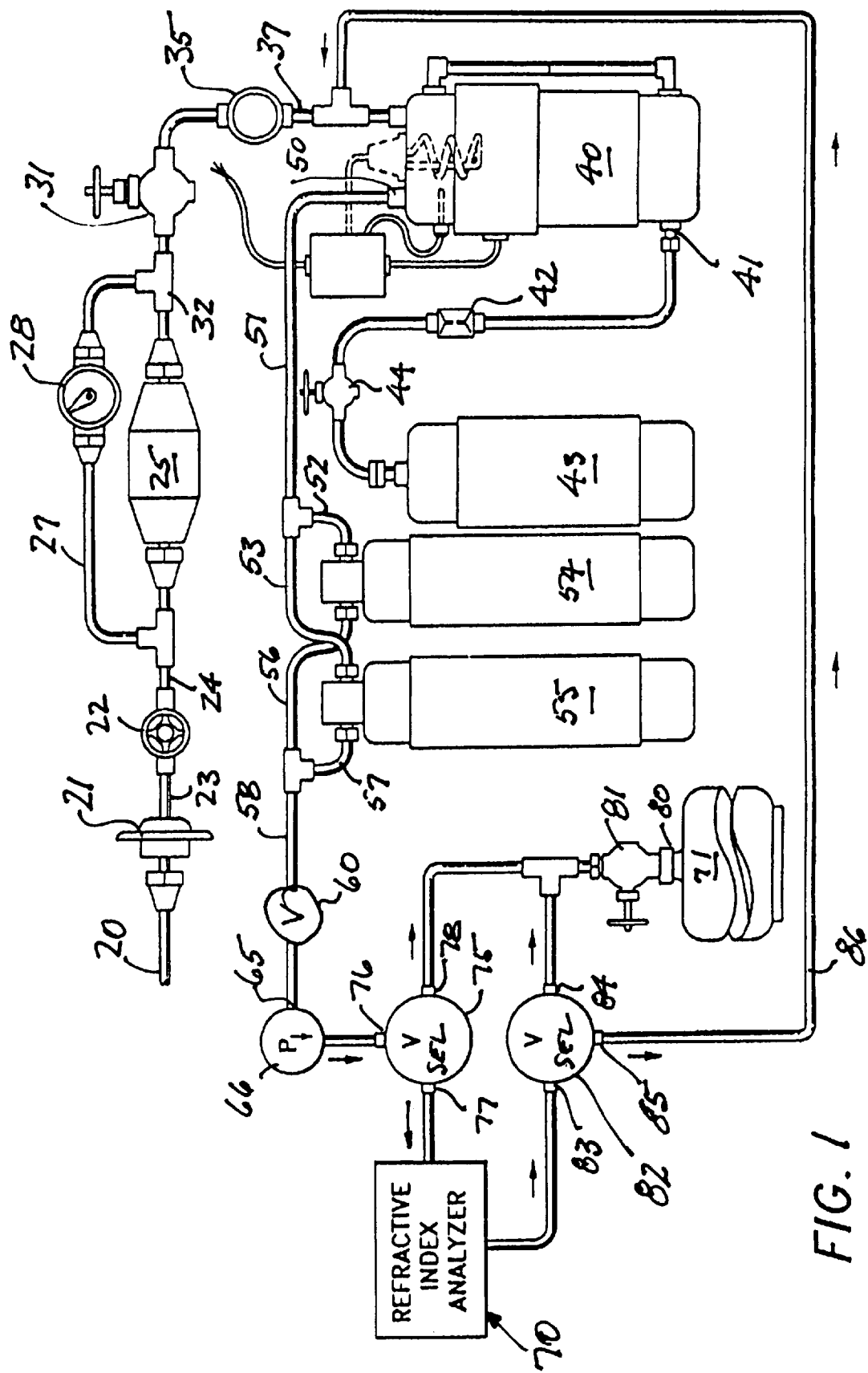
FIG. 1, the only figure, is a schematic drawing showing the circuitry of this invention.

Inlet pipe 20 from a machine (not shown) whose refrigerant is to assayed is separably joined to an inlet fitting 21 of the system of this invention. An on-off valve 22 is connected to a hose 23 from the fitting and to a hose 24, thereby to control entry of fluid into the system.

A filter/deacidifier 25 is connected to hose 24. It is a conventional cartridge type which removes particulate matter, and neutralizes acids of the type customarily found in used refrigerants.

At this point, Burke U.S. Pat. No. 6,260,372 is incorporated by reference herein in its entirety for its showing of useful elements of this system, upstream from the analyzer. The reader will notice the similarities to FIG. 3 of that patent.

A bypass conduit 27 is connected across the filter de-acidifier. It includes shut-off valve 28. This arrangement, coupled with protective valves, enables the filter/acidifier to be by-passed if desired.

A liquid/vapor valve 31 is connected at the downstream end of the filter/de-acidifier and the by-pass at a T joint 32. The liquid-vapor valve is adapted to pass either gas or liquid. It is further connected to the inlet of a sight glass 35. The sight glass enables the viewer to ascertain whether liquid or gas is flowing through the system at this point.

A conduit 37 receives fluid from the sight glass and conveys it to a tank-type oil separator 40. Oil settles to the bottom of the tank from which it is withdrawn through outlet 41, passes through a flow control 42 and enters an oil recovery tank 43. An off-on oil drain valve 44 controls flow of oil to tank 43.

Refrigerant fluid in whatever phase is withdrawn from the top of the oil separator through outlet 50. It flows through conduit 51 to two branches 52, 53, each of which enters a respective filter/dryer tank 54, 55.

Outlet conduits 56, 57 are joined to a discharge conduit 58. Conduit 58 is connected to an off-on discharge valve 60. This is the ultimate control valve for the active system.

Inlet 65 of a pressure pump 66 is connected to the outlet end of the discharge valve. When in operation, it withdraws fluid from the upstream system and pressurizes it so as to be certain that the fluid is in the liquid phase.

A refractive index analyzer 70 of any suitable type is plumbed into this system downstream from the pump. It is intended to receive sample material for analysis. After the sample has been analyzed, it must still remain captive. For this purpose a recovery tank 71 is provided. This recovery tank may also be used when the entire system is to be purged, as will become evident.

A first selector valve 75 has an inlet 76 connected to the outlet of the pump. It has two selectible ports 77, 78. The first port 77 is connected to the inlet of the analyzer. The second port 78 is connected to the inlet port 80 of the recovery tank through a shut-off valve 81.

A second selector valve 82 has an inlet port 83 and selectible outlet ports 84, 85. It also has a shut-off condition in which no flow is allowed. Port 84 is connected to the recovery tank inlet. Port 85 is optional. When used, it is connected to an optional return line 86, which extends to the inlet of the oil separator. As will be seen, the return line is optional, and in the simplest embodiment, valve 82 has only two settings, one to close the valve and the other to permit flow to the recovery tank.

The operation of this system is straight forward. With appropriate valves open or closed, and the pump in operation, a liquid sample is collected in the analyzer and analyzed. When analysis is completed, the sample is discharged to the recovery tank. Alternatively it may be returned to the oil separator, in which event it will remain in the system. The assay will be repeated for sequential analyses on the same system, or will later be used on other machines. In that event, the device will be purged of the residue gases (which will be caught in the recovery tank), or back to the refrigeration machine system from which it originally came from before the next sample is secured.

This invention is not to be limited by the embodiment shown in the drawing and described in the description, which is given by way of example and not of limitation, but only in accordance with the scope of the appended claims.

I claim:

1. A system for sampling and assaying refrigerant fluid from a refrigerating machine, said system comprising:

an inlet to receive refrigerant fluid from said machine;

a control valve to enable or to prevent flow of refrigerant into the system from said inlet;

a filter/deacidifier for removing particles and acids from said fluid;

an oil separator to remove oil from said fluid;

an oil recovery tank for receiving oil from said separator;

a filter/dryer receiving fluid which has passed through said filter/deacidifier and said oil separator;

a pump receiving fluid which has passed through said filter/dryer, said pump delivering said refrigerant in its liquid state;

a first selector valve having an inlet port receiving said liquid refrigerant from said pump;

a refractive index analyzer having an inlet and an outlet;

a recovery tank;

said first selector valve being so constructed as selectively to direct fluid from its said inlet port to said inlet port of said analyzer or to said recovery tank;

a second selector valve having an inlet port connected to said outlet port of said analyzer and a first outlet port connected to said recovery tank, and having a selectible closed position preventing flow through said second selector valve;

said refractive index analyzer having the capacity to assay the contents of a sample for the purpose of learning the identity and proportions of the refrigerant gases in said sample, utilizing refractive index techniques on a liquid sample;

said sample being prepared by directing liquid sample through the first selector valve into the analyzer while said second selector valve is closed;

said sample being removable from said analyzer by opening said second selector to permit flow into said recovery tank.

2. A system according to claim 1 in which a return conduit extends from a second port on said second selector valve to said oil separator, said second selector valve having a further setting to enable this flow to occur.

3. A system according to claim 1 in which a shut-off valve is provided on said recovery tank to enable removal and replacement of a recovery tank.

* * * * *